United States Patent [19]

McRae

[11] Patent Number: Plant 6,373

[45] Date of Patent: Nov. 8, 1988

[54] LILY PLANT NAMED 'PANTOMIME'

[75] Inventor: Edward A. McRae, Boring, Oreg.

[73] Assignee: Melridge, Inc., Aurora, Oreg.

[21] Appl. No.: 929,322

[22] Filed: Nov. 10, 1986

[51] Int. Cl.[4] ..... A01H 5/00

[52] U.S. Cl. ..... Plt./68

[58] Field of Search ..... Plt. 68

*Primary Examiner*—James R. Feyrer

*Attorney, Agent, or Firm*—Charles W. Rummler

[57] ABSTRACT

A new variety of Oriental hybrid lily plant bearing large upright-facing flowers particularly characterized by their clear pink coloration with deeper midribs, their large size and substance, and their upright to semi-upright orientation, the flowers being of excellent form and long persistence both on the plant and as cut flowers. This combination is completely new in the Oriental hybrid divisions of lilies suited to forcing and to mass commercial cultivation. The plant is an excellent garden plant, highly resistant to disease and shows tolerance of virus; the bulbs may be precooled and forced for cut flower production and the clone is vigorous, a good grower and a good propagator.

BACKGROUND OF THE INVENTION

This new variety of lily plant originated as a seedling which first flowered at Sandy, Oreg., in 1970, from breeding efforts which had as their objective the production of large flowered, upright and semi-upright Oriental hybrids in shades of pink and white, suited to forcing into flower out of season, heretofore unknown in the lily breeding art.

I achieved the desired objective in this case by using as the seed parent a selected clone from the strain 'Pink Glory' and as the pollen parent a selected form of the species *Lilium nobilissimum.* In order to cross these distantly related lilies successfully, it was necessary to maintain extremely high greenhouse temperatures for one week after pollination.

1 Drawing Sheet

The flowers of this new lily variety are characterized by an upright to semi-upright orientation, extremely large size and broad tepalled bowl-shaped form, unusually thick substance and a distinctive clear pink coloration with richer magenta-rose midribs, unique among Oriental hybrid lilies. This plant possesses unusually strong, stout stems with exceptionally broad leaves and in addition, possesses to a high degree the desirable characteristics of hybrid vigor, great hardiness and disease resistance. The clone also possesses all of the desired characteristics of excellence of form, color and habit and is a vigorous and good grower and propagator, as observed at Sandy, Oreg. This new plant is well suited to forcing out of season when the bulbs are dug at the appropriate time and properly precooled; late October-dug bulbs, properly precooled and potted in January, will flower under glass in western Oregon, with no supplementary lighting and at moderate greenhouse temperatures, in an average of 100 to 115 days. This new variety of lily plant has been asexually reproduced by me and under my direction at Sandy, Oreg., and successive generations, produced by natural propagation from bulblets, by bulb scale propagation, and by tissue culturing from bulb scale explants, have demonstrated that the novel and distinctive characteristics of this new variety are fixed and hold true under asexual propagation from generation to generation.

DESCRIPTION OF THE DRAWING

My new variety of lily plant is illustrated by the accompanying photographic drawing which shows, in full color, a three-quarter face view of a mature flower, the colors shown being as nearly true to those specified herein as is reasonably possible to obtain by conventional photographic procedures.

DESCRIPTION OF THE NEW VARIETY

The following is a detailed description of my new variety of Oriental hybrid lily with nomenclature according to The International Lily Register of The Royal Horticultural Society of London, England (Second Edition, 1969), and with color designations according to The R.H.S. Colour Chart published by The Royal Horticultural Society in 1966.

THE PLANT

Origin: Seedling.

Parentage:

*Seed parent.*—A selected clone from the 'Pink Glory' strain, unnamed and unpatented.

*Pollen parent.*—A selected clone of *Lilium nobilissimum,* unnamed and unpatented.

Classification:

*Horticultural.— Division VII-B, Bowl-shaped Oriental Hybrid Lily, according to The Horticultural Classification of Lilies by The Royal Horticultural Society of London, England.*

*Commercial.*—Hybrid Oriental Lily.

Form: Single stem, tall, erect and stately.

Height: From 70 to about 125 cm., from bulbs of about 14 to 18 cm. in circumference, provided their light levels are adequate. Low light levels may cause "stretching".

Growth: Vigorous and upright.

Foliage:

*Quantity.*—Abundant.

*Leaf size.*—Unusually broad, and about 12 to 15 cm. long.

*Leaf shape.*—Lanceolate with acuminate apex.

*Texture.*—Leathery.

*Appearance.*—Glossy.

*Color.*—Medium green, lighter on the lower side.

Bulbs:

*Size.*—Various, ranging to 25 cm. in circumference in commercial use.

*Color.*—White, with flushes of soft pink or soft yellow after exposure to light.

THE BUD

Form: Long, ovoid and obtuse.

Size: About 9 to 12 cm. long and about 10 to 12 cm. in circumference just prior to opening.

Opening rate: The bud opens slowly, taking about an hour in response to morning light.

Color: Red-purple, 65C-D, with soft green midribs.

Peduncle:

*Length.*—Averages about 4 to 6 cm. It may elongate if light levels are too low or if the bulbs have been improperly stored prior to forcing.

*Color.*—Medium green with very light plum overlay.

THE FLOWER

Blooming habit: Once annually and profusely in midseason for Oriental lilies.

Size: Large, averaging about 18 to 23 cm. in diameter, reflexing at the tepal tips on the second day to about 15 to 18 cm. in diameter.

Borne: In a single racemose inflorescence producing 3 to 6 flowers from a bulb of about 14 to 16 cm. in circumference.

Shape: Broad bowl-shaped by the second day with the bowl being about 10 cm. deep.

Tepalage:

*Number.*—Six.

*Arrangement.*—Hexagonal and imbricated.

*Shape.*—Broad ovate. Outer tepals are about 3 to 3.5 cm. wide and the inner tepals are about 5 to 5.5 cm. wide.

*Appearance.*—Shiny.

*Color.*—Clear pink, 65A, shading to 64D toward the midrib and the midrib of each tepal is a deeper magenta-rose, 64B-C. The pink color suffuses toward the margins of the tepals becoming only slightly lighter, 65B.

*Tepal spotting.*—The flowers are unspotted.

*Color changes.*—The flowers become slightly lighter adding a more lavender tone to pink approaching 65A-C as the flowers age. Low light levels and extreme heat may cause the pink pigmentation to decrease. The nectary furrows are apple green.

Pedicel:

*Length.*—About 8 to 12 cm., in average.

*Form.*—Sturdy and ascending up to about 46° from the horizontal.

*Color.*—Medium green with very light plum overlay.

Persistence: The tepals stay on the stems about 3 weeks.

Fragrance: None

Disease resistance: The flower and plant are resistant to disease; in particular, they are resistant to Botrytis blight and to Fusarium bulb rot.

Lasting quality: The flower is long lasting, both on the plant and as a cut flower.

THE REPRODUCTIVE ORGANS

Stamens:

*Number.*—Six.

*Arrangement.*—Typical of the genus Lilium.

*Anthers (dehisced) and pollen.*—Color: Greyed red, 179A.

*Filaments.*—Length: About 5 cm. Color: Soft green to white.

Pistils:

*Number.*—One.

*Style.*—Length: About 5 cm.

*Stigma.*—Size: Large. Color: Soft greenish white to very light pink.

Character of ovary: Characteristic of genus Lilium.

THE FRUIT

Fertility: The fruit is fertile.

Shape: Ovoid.

Color at maturity: Soft brown, sometimes overlaid with soft plum.

My new variety of Oriental hybrid lily most nearly resembles 'Pink Glory' but it has much larger and thicker and more bowl-shaped flowers which are upright to semi-upright rather than side facing in orientation, and its flowers are completely unspotted. The flowers of this new variety are distinguished by their deeper magenta-rose midribs and its leaves are much broader and its stems are stronger and stockier than those of 'Pink Glory'.

I claim:

1. A new and distinct variety of Oriental hybrid lily plant, substantially as herein shown and described, characterized by its unique upright to semi-upright flowers with their pink coloration, deeper magenta-rose midribs and complete lack of spotting, the plant has a vigorous growth habit and rapid natural propagation and is characterized by the excellence of its flower form, size and substance, its versatility both as a garden plant and as a cut flower producer, and its high resistance to diseases.

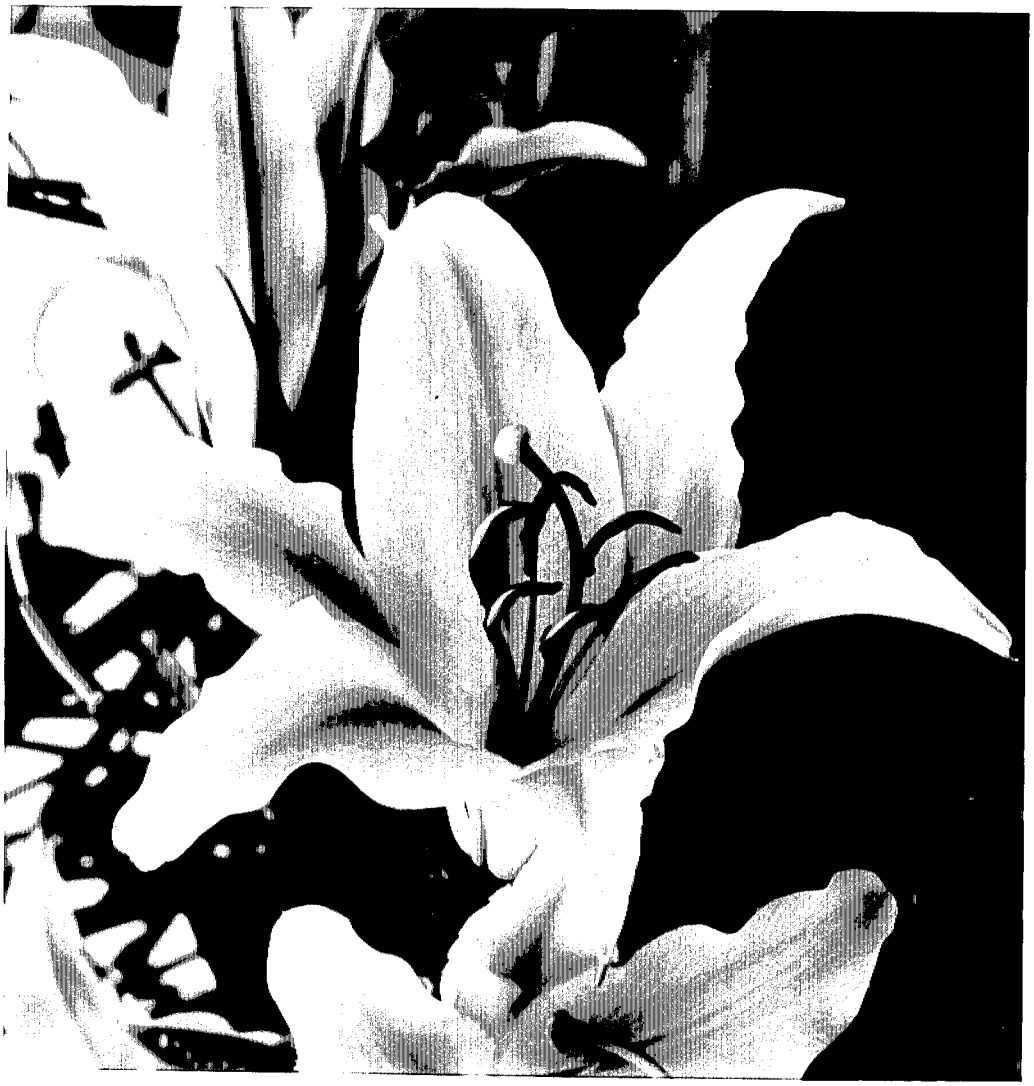

* * * * *